(12) United States Patent
Kennedy, II et al.

(10) Patent No.: US 6,694,169 B2
(45) Date of Patent: Feb. 17, 2004

(54) TARGETING SYSTEM AND METHOD OF TARGETING

(75) Inventors: Kenneth C. Kennedy, II, Orchard Park, NY (US); John C. McNeirney, Fairburn, GA (US)

(73) Assignee: Minrad Inc., Buffalo, NY (US)

( * ) Notice: Subject to any disclaimer, the term of this patent is extended or adjusted under 35 U.S.C. 154(b) by 28 days.

(21) Appl. No.: 09/792,191

(22) Filed: Feb. 22, 2001

(65) Prior Publication Data

US 2002/0115932 A1 Aug. 22, 2002

(51) Int. Cl.[7] .................................................. A61B 5/05
(52) U.S. Cl. ...................... 600/426; 600/407; 600/427; 378/65; 378/206
(58) Field of Search ................................ 600/426, 427; 606/130; 378/206, 64, 65; 356/399

(56) References Cited

U.S. PATENT DOCUMENTS

| | | |
|---|---|---|
| 3,628,021 A | 12/1971 | MacDonald |
| 3,629,594 A | 12/1971 | Sandberg |
| 4,012,638 A | 3/1977 | Altschuler et al. |
| 4,117,337 A | 9/1978 | Staats |
| 4,158,776 A | 6/1979 | Barrett |
| 4,167,675 A | 9/1979 | Stödberg et al. |
| 4,203,037 A | 5/1980 | Gur et al. |
| 4,223,227 A | 9/1980 | Horwitz |
| 4,259,585 A | 3/1981 | Novak et al. |
| 4,287,425 A | 9/1981 | Elliott, Jr. |
| 4,296,329 A | 10/1981 | Mirabella |
| 4,356,400 A | 10/1982 | Polizzi et al. |
| 4,385,397 A | 5/1983 | Verro |
| 4,406,015 A | 9/1983 | Koga |
| 4,426,726 A | 1/1984 | Cheetham |
| 4,521,905 A | 6/1985 | Hosokawa |
| 4,563,768 A | 1/1986 | Read et al. |
| 4,578,806 A | 3/1986 | Grass et al. |
| 4,599,738 A | 7/1986 | Panetta et al. |
| 4,651,732 A | 3/1987 | Frederick |
| 4,727,565 A | 2/1988 | Ericson |
| 4,730,350 A | 3/1988 | Albert |
| 4,750,487 A | 6/1988 | Zanetti |
| 4,821,727 A | 4/1989 | Levene et al. |
| 4,836,671 A | 6/1989 | Bautista |
| 4,930,143 A | 5/1990 | Lundgren et al. |
| 5,013,317 A | 5/1991 | Cole et al. |
| 5,031,203 A | 7/1991 | Trecha |
| 5,040,872 A | 8/1991 | Steinle |
| 5,053,042 A | 10/1991 | Bidwell |
| 5,056,129 A | 10/1991 | Steinmeyer |
| 5,056,523 A | 10/1991 | Hotchkiss, Jr. et al. |
| 5,078,142 A | 1/1992 | Siczek et al. |
| 5,083,570 A | 1/1992 | Mosby |
| 5,107,843 A | 4/1992 | Aarnio et al. |
| 5,116,344 A | 5/1992 | Sundqvist |
| 5,155,623 A | 10/1992 | Miller et al. |
| 5,157,533 A | 10/1992 | Hanamoto |
| 5,209,232 A | 5/1993 | Levene |
| 5,212,720 A | 5/1993 | Landi et al. |
| 5,283,808 A | 2/1994 | Cramer et al. |
| 5,316,014 A | 5/1994 | Livingston |
| 5,320,111 A | 6/1994 | Livingston |
| 5,463,669 A | 10/1995 | Kaplan |

(List continued on next page.)

*Primary Examiner*—Dennis Ruhl
*Assistant Examiner*—Barry Pass
(74) *Attorney, Agent, or Firm*—Hodgson Russ LLP

(57) ABSTRACT

An embodiment of the targeting system includes a penetrating beam emitter, a penetrating beam receiver, and a targeting assembly. The targeting assembly is adjustable. The targeting assembly has a targeting marker in a path of a penetrating beam provided by the emitter. The targeting marker is at least partially opaque to a penetrating beam emitted by the emitter, and the targeting marker indicates a targeting point on a target axis. The targeting assembly further includes a targeting beam device capable of providing a targeting beam along the target axis.

95 Claims, 15 Drawing Sheets

U.S. PATENT DOCUMENTS

| | | |
|---|---|---|
| 5,499,989 A | 3/1996 | LaBash |
| 5,537,453 A | 7/1996 | Williams et al. |
| 5,553,115 A | 9/1996 | Odaka et al. |
| 5,572,568 A | 11/1996 | Kanemitsu |
| 5,598,269 A | 1/1997 | Kitaevich et al. |
| 5,644,616 A * | 7/1997 | Landi et al. ................ 378/206 |
| 5,810,841 A | 9/1998 | McNeirney et al. |
| 6,104,779 A * | 8/2000 | Shepherd et al. ............. 378/65 |

* cited by examiner

FROM FIG. 11B

↓

| DETERMINE THE LOCATION OF THE CENTER OF EMANATION. | —233 |

TARGETING SYSTEM AND METHOD OF TARGETING

BACKGROUND OF THE INVENTION

1. Field of the Invention

The present invention relates generally to systems and methods of targeting. For example, the present invention may be used to target areas residing behind a surface.

2. Discussion of Related Art

In the prior art, U.S. Pat. No. 5,320,111 and U.S. Pat. No. 5,316,014 disclose a method and apparatus for locating and guiding a biopsy needle with respect to an X-rayed specimen having a tumor to be engaged by the needle. Intersecting laser beams are utilized to mark the location of the tumor and to guide the biopsy needle in a vertical path. The laser beam source is movable in orthogonal paths while compensating means redirect the beams to maintain them within a target area or eliminate any parallax. That is, the angular position of the laser light beam is adjusted to different angles at different coordinate positions to have the needle follow along a portion of a straight line path from the X-ray point source through the lesion and to the X-ray film. Thus, the needle tip should not be displaced to one side of a small lesion.

Such prior art systems and methods have disadvantages. For instance, they are difficult to accurately and quickly calibrate.

SUMMARY OF THE INVENTION

The present invention includes a targeting system having a penetrating beam emitter, a penetrating beam receiver, and an adjustable targeting assembly. The targeting assembly has a targeting marker in the path of a penetrating beam emitted by the emitter. The targeting marker is at least partially opaque to the penetrating beam emitted by the emitter, and the targeting marker indicates a targeting point on a target axis. The targeting assembly further includes a targeting beam device that is capable of providing a targeting beam along the target axis.

In addition, the present invention includes a method of calibrating a targeting system, such as the system described above, and a method of targeting an area of interest.

BRIEF DESCRIPTION OF THE DRAWINGS

For a fuller understanding of the nature and objects of the invention, reference should be made to the following detailed description taken in conjunction with the accompanying drawings, in which:

FIGS. 11A, 11B and 11C show a method of calibrating a system according to the present invention.

DETAILED DESCRIPTION OF THE INVENTION

Figure 1:
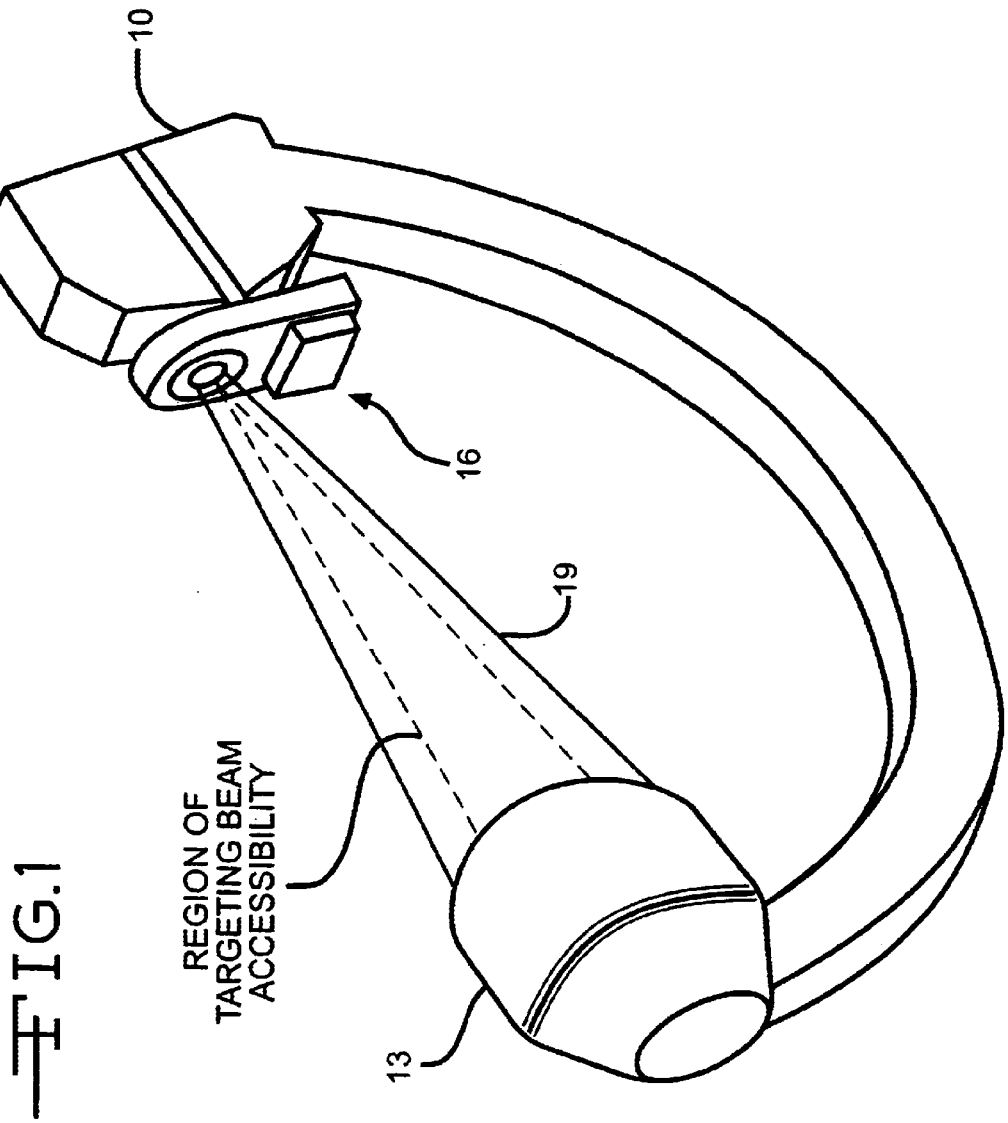
FIG. 1 is a perspective view of a system according to the present invention.
Figure 2:
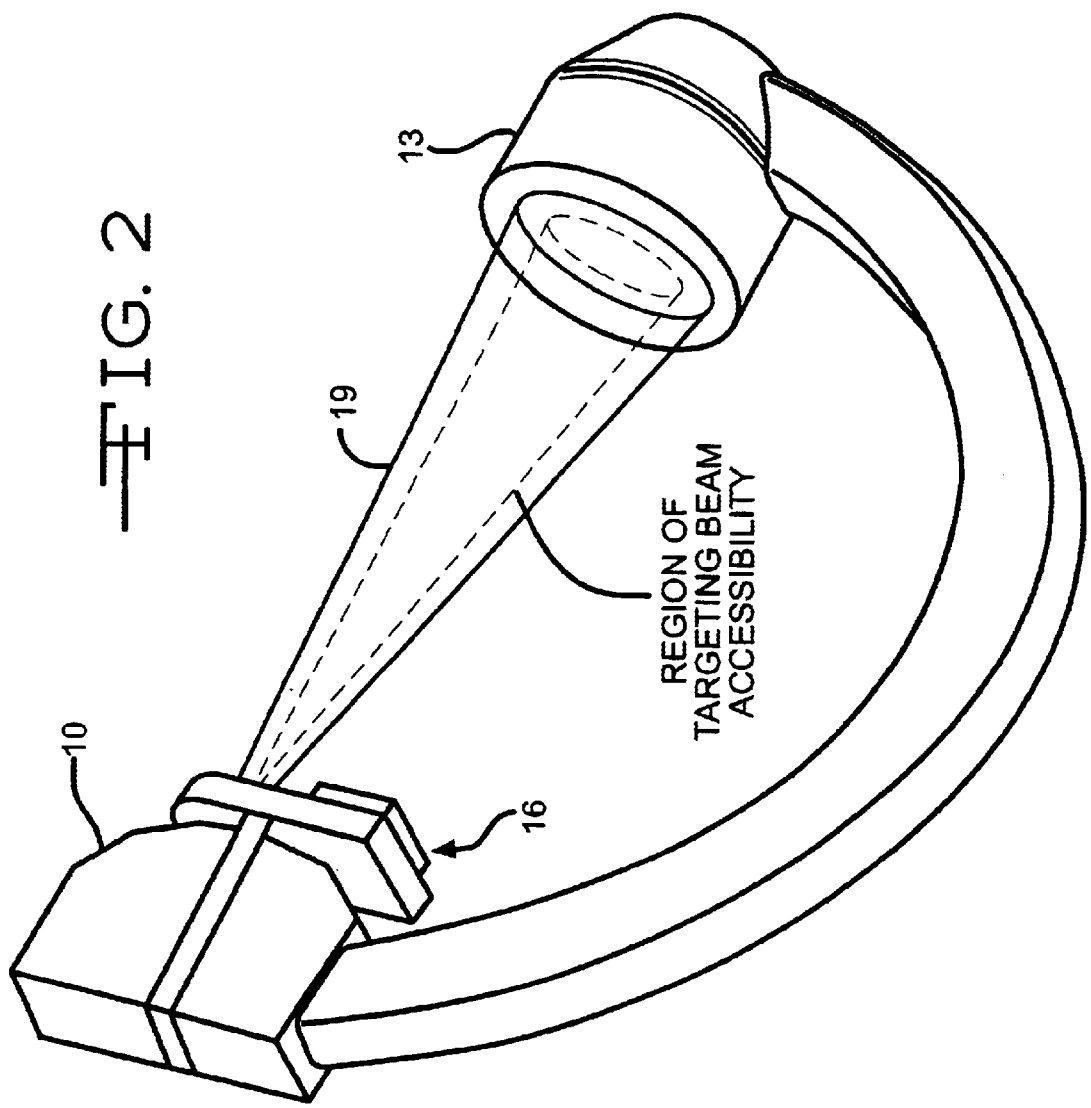
FIG. 2 is another perspective view of the system shown in FIG. 1.
Figure 3:
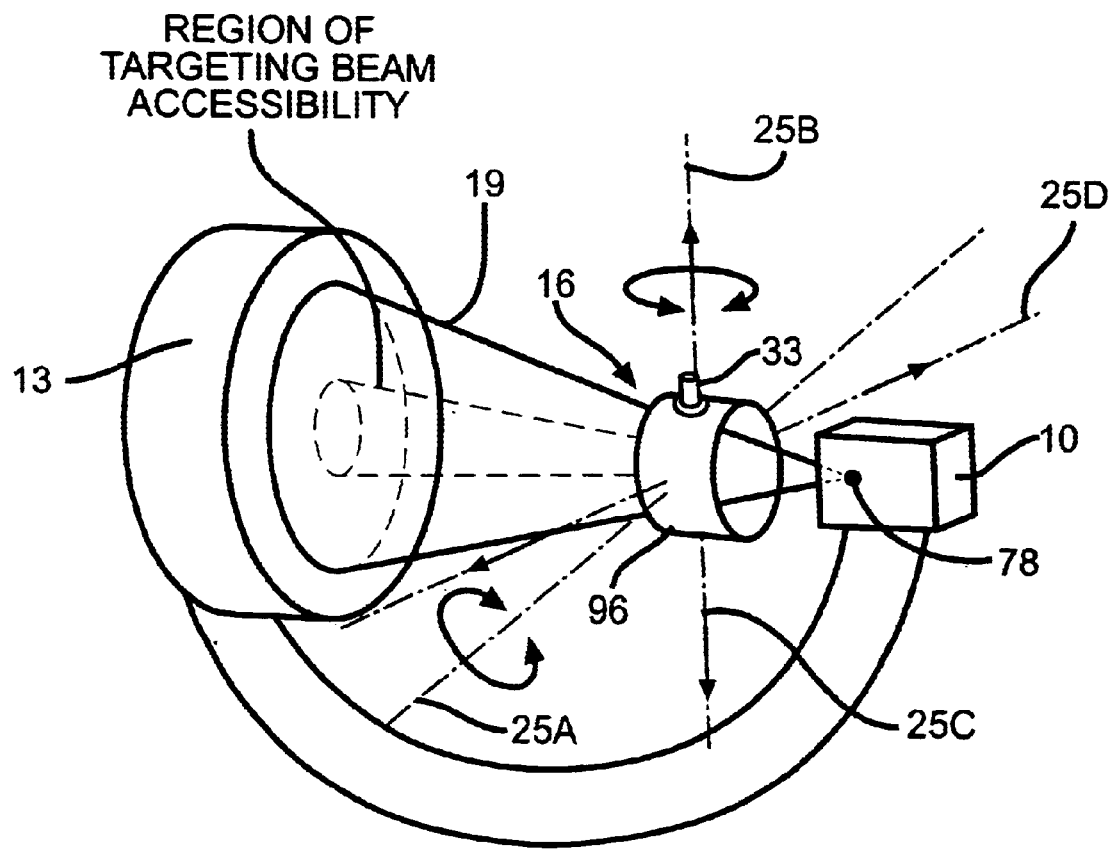
FIG. 3 is a schematic perspective view of the systems shown in FIGS. 1 and 2 showing part of the targeting assembly.
Figure 4:
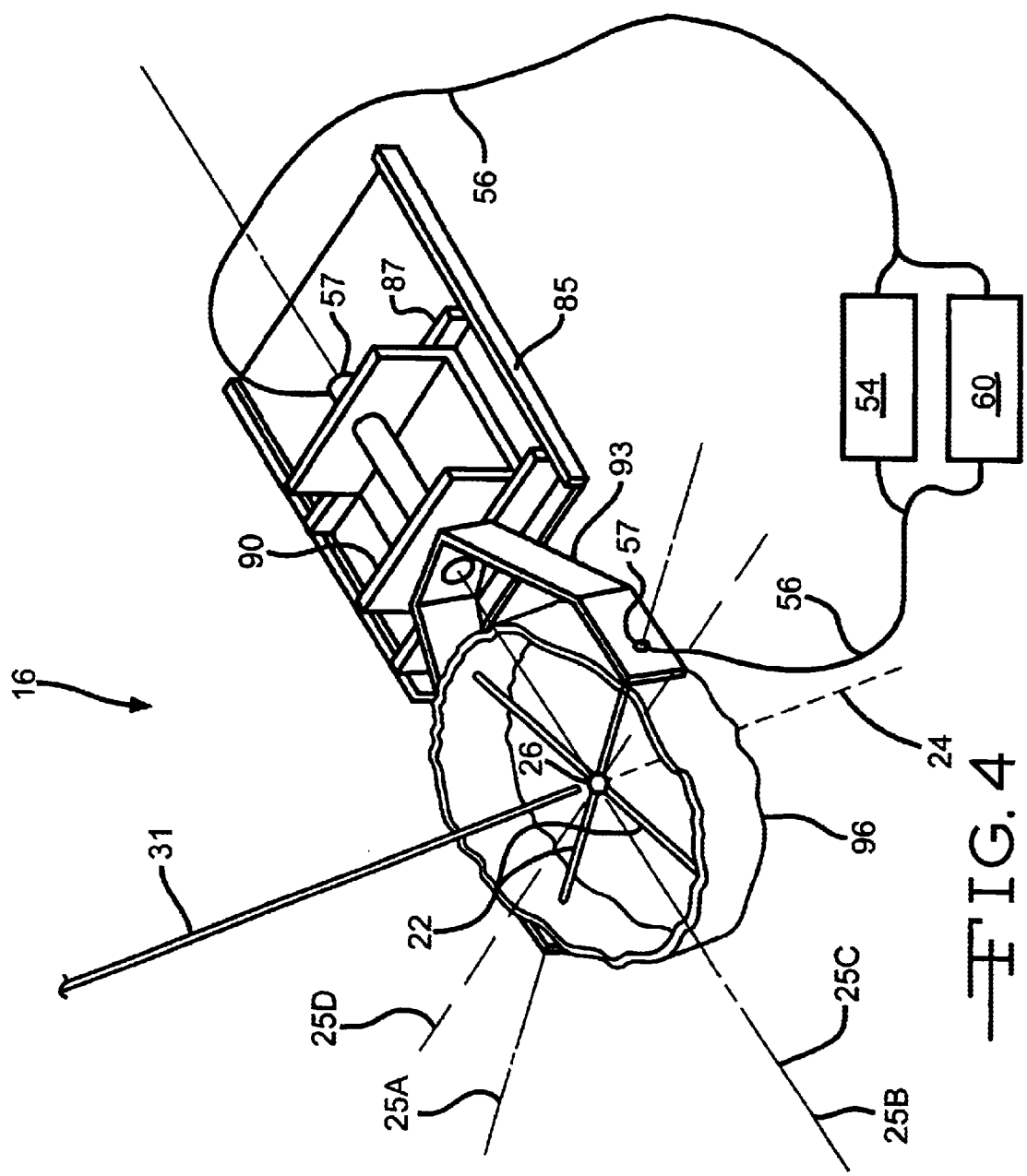
FIG. 4 is a schematic perspective view of part of a targeting assembly according to the present invention.

FIGS. 1 and 2 show a system according to the present invention. The system shown in FIGS. 1 and 2 has a penetrating beam emitter 10, a penetrating beam receiver 13 and a targeting assembly 16. FIG. 3 is a schematic of the system shown in FIGS. 1 and 2, depicting only part of the targeting assembly 16 for clarity. FIG. 4 shows another part of the targeting assembly 16 according to an embodiment of the present invention.

FIGS. 1 through 3 show a path of a penetrating beam 19 sent from the penetrating beam emitter 10 to the penetrating beam receiver 13. The penetrating beam emitter 10 may include a source of the penetrating beam 19 commonly referred to as a point source 78. The penetrating beam emitter 10 may emit x-rays, for example. The penetrating beam receiver 13 may be an image intensifier. An example of a device having an x-ray emitter and image intensifier is a fluoroscope such as model number 9800, manufactured by OEC Medical Systems Inc. located in Salt Lake City, Utah.

The targeting assembly 16 allows a target axis 24 to be moved in four degrees of freedom. For example, components of the targeting assembly may be translatable in two directions and rotatable about two axes, as shown by arrows in FIG. 3 and described in more detail below. The translatable directions may be perpendicular to each other. The axes of rotation may be perpendicular to each other.

The targeting assembly 16 includes a targeting marker 22 between the emitter 10 and the receiver 13 in the path of the penetrating beam 19. The targeting marker 22 is at least partially opaque to the penetrating beam 19 emitted by the emitter 10. If the penetrating beam 19 is an x-ray, the targeting marker 22 may be, for example, two perpendicular wires of x-ray opaque material, such as lead. The targeting marker 22 indicates a targeting point 26 on a target axis 24 (see FIGS. 4 and 5). For example, if the targeting marker 22 is comprised of two perpendicular wires, the targeting point 26 would be the point at which the perpendicular wires would intersect, if they were extended to intersect. In one embodiment of the present invention, the targeting point 26 is on a pair of rotational axes 25A, 25B and on a pair of translational axes 25C, 25D of the targeting assembly 16 (see FIGS. 3 and 4).

The targeting assembly 16 further includes a targeting beam device 28 (FIG. 5) capable of providing a targeting beam 31 along a target axis 24. The targeting beam 31 may be a laser beam, and the targeting beam device 28 may include a laser 33 such as model number EIL-650-03-3C manufactured by Laser Photonics Technology, Inc., located in Amherst, N.Y. The arrangement shown in FIG. 5 may be used with the device shown in FIG. 4, and a combination is shown in part in FIG. 3. The targeting beam 31 and target axis 24 are depicted in FIG. 4, but the targeting beam device 28 is omitted from FIG. 4 for clarity.

Figure 5:
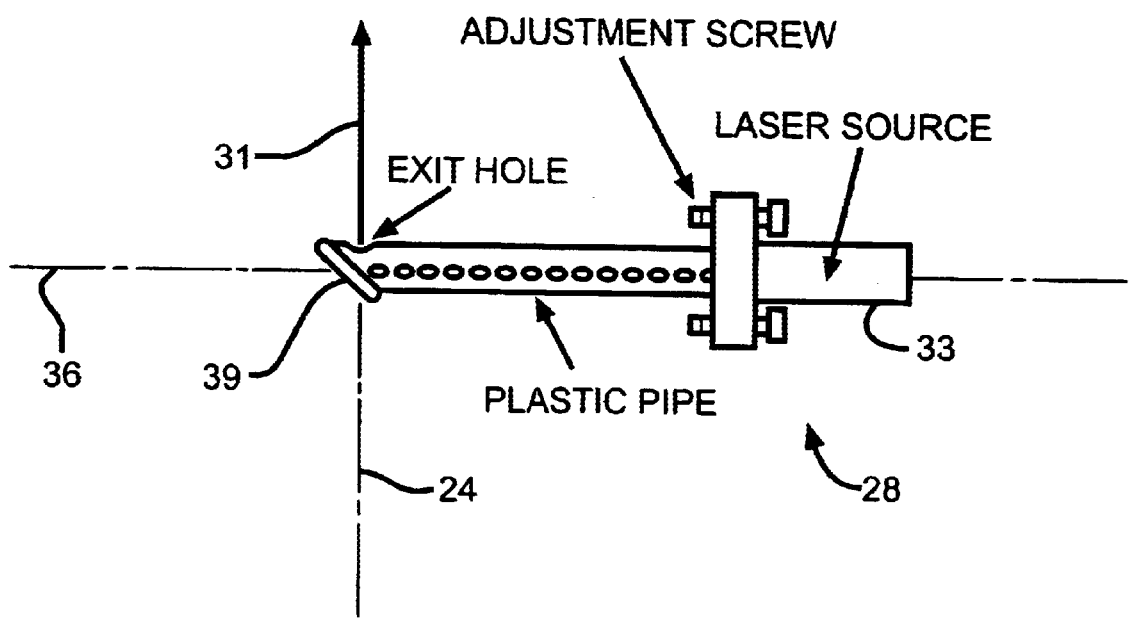
FIG. 5 is a schematic diagram of a targeting beam device.

As shown in FIG. 5, part of the targeting beam device 28 may be positioned on a second axis 36 and the targeting beam device 28 may further include a mirror 39 positioned on the first and second axes 24, 36. The mirror 39 is angled to receive the targeting beam 31 along the second axis 36 and to reflect the targeting beam 31 along the target axis 24. The mirror 39 may be at least partially translucent to the penetrating beam 19. If the mirror 39 is not at least partially translucent to the penetrating beam 19, the mirror 39 may be made relatively small so that it does not block the penetrating beam in a manner that prevents a person viewing the image of the targeting marker produced via the penetrating beam receiver from distinguishing the location of the targeting point 26.

Figure 6:
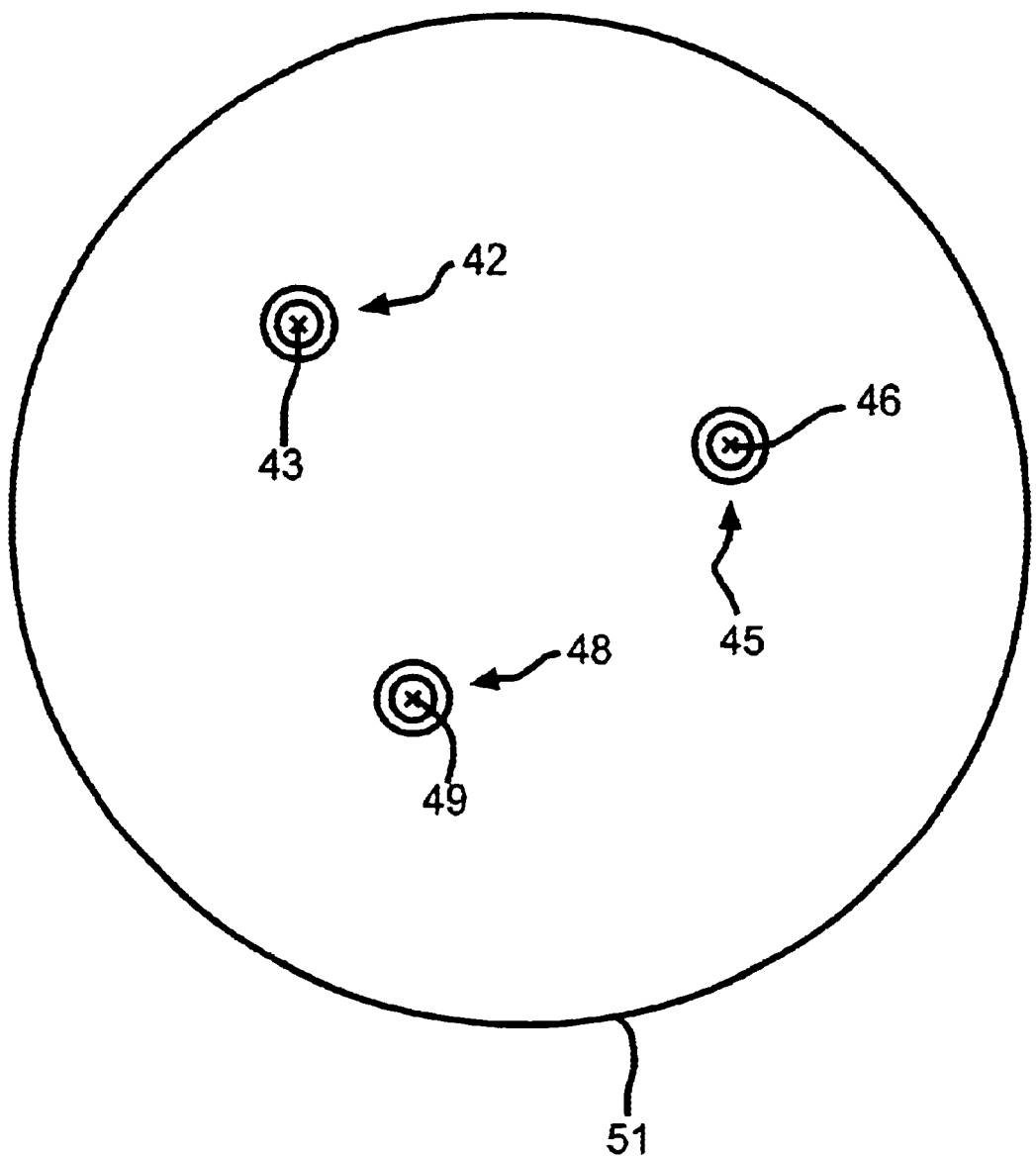
FIG. 6 is a pad having three calibration targets thereon.
Figure 7:
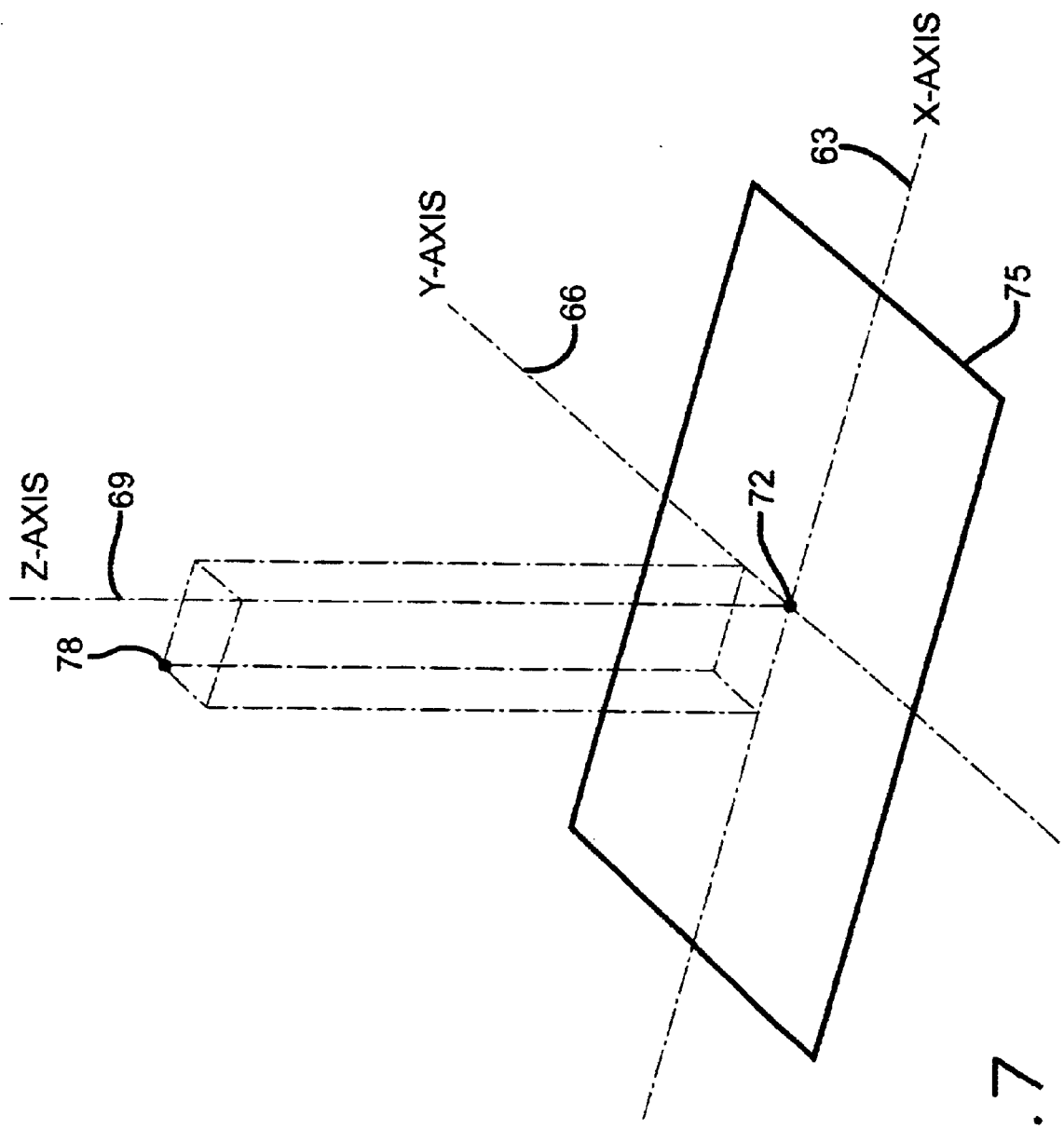
FIGS. 7 through 10 are perspective views illustrating underlying concepts of the present invention.
Figure 8:
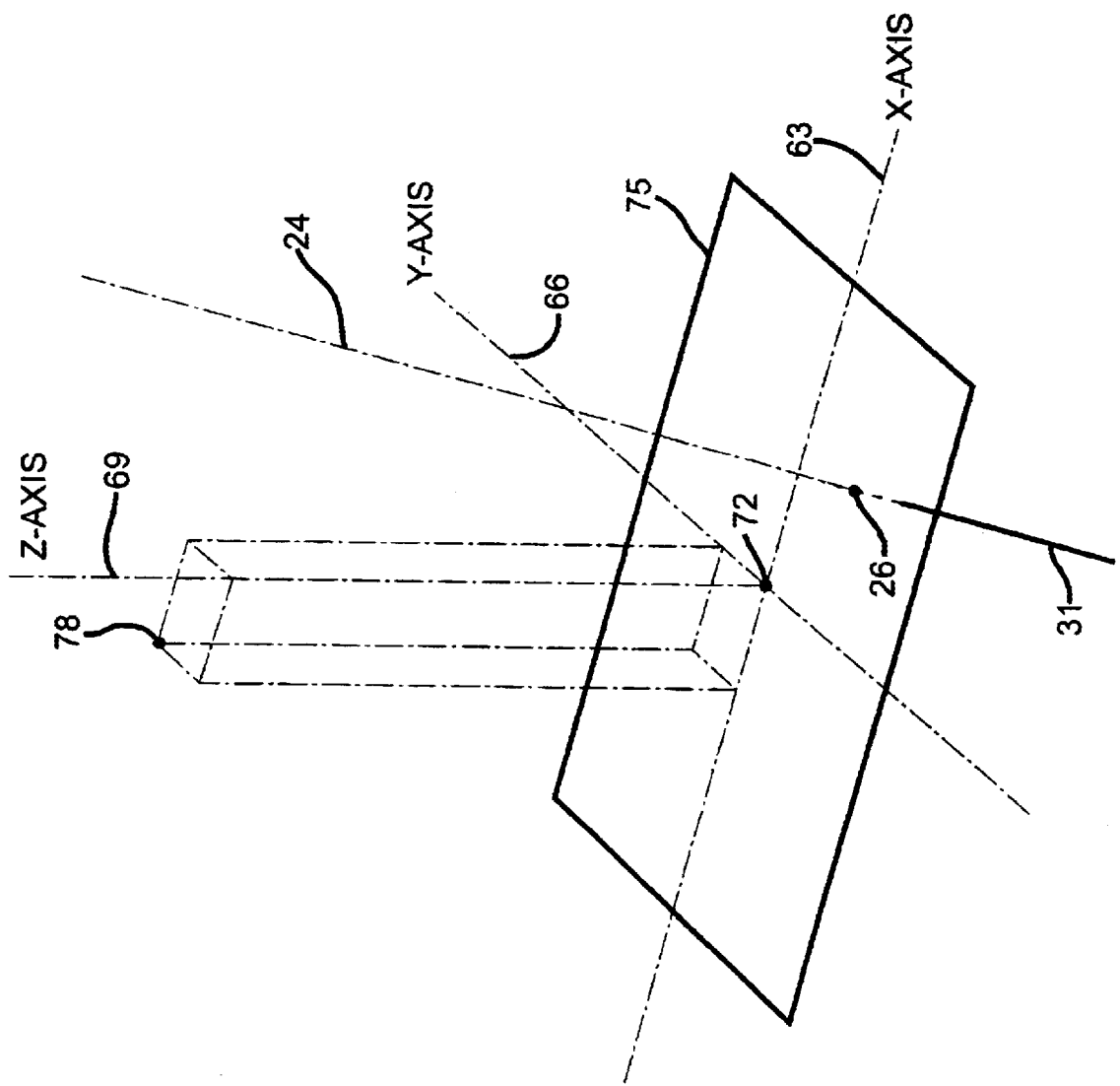
Figure 9:
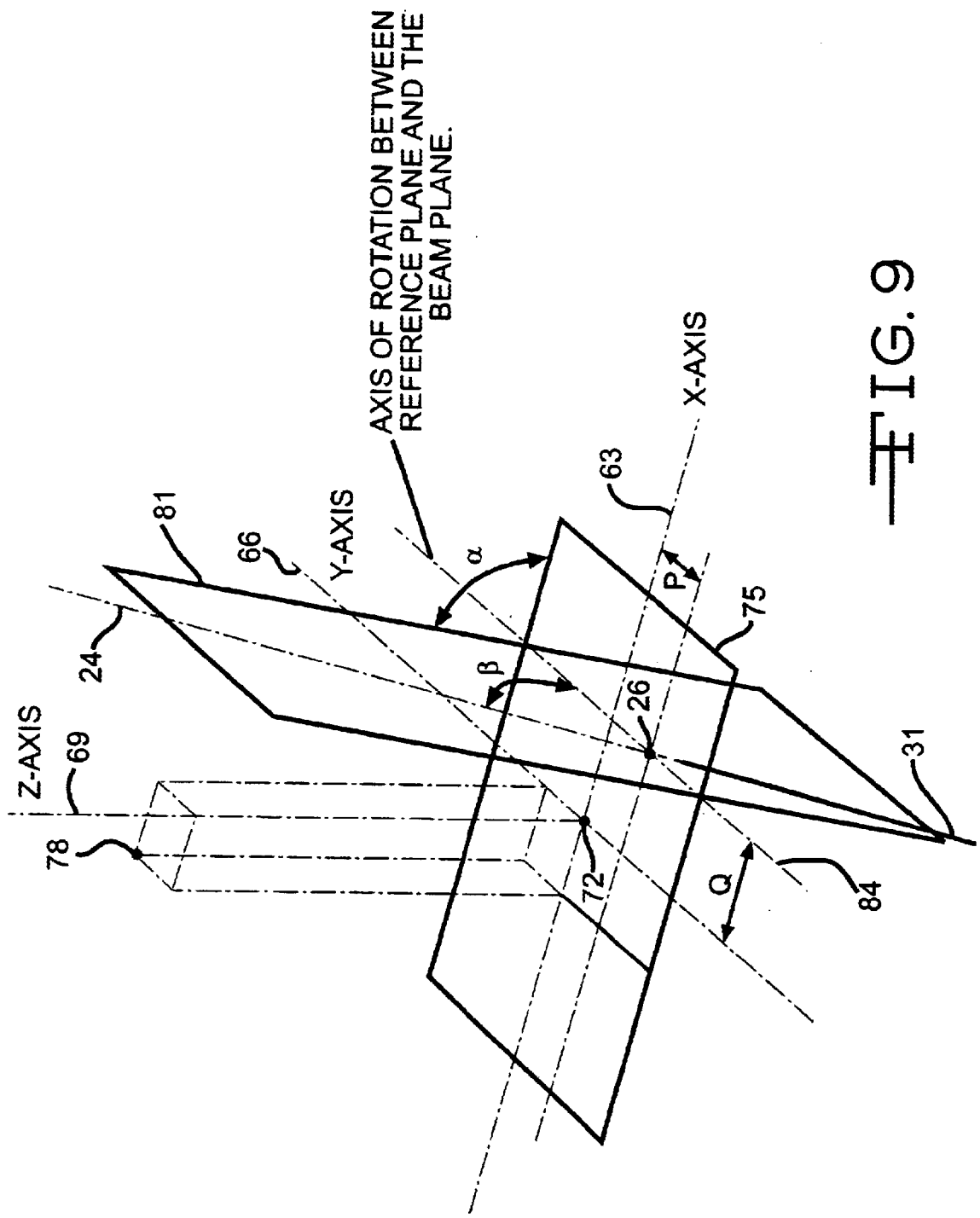

As shown in FIG. 6, the invention includes at least one calibration target 42 indicating a calibration point 43. To calibrate the present invention, the calibration target 42 is located in the path of the penetrating beam 19. For example, the calibration target 42 may be placed on the receiver 13. The calibration target 42 is at least partially opaque to the penetrating beam 19. A second and a third calibration target 45, 48 may be disposed in the path of the penetrating beam 19, for example between the emitter 10 and the receiver 13 at a second and third location, respectively. The second and third calibration targets 45, 48 are at least partially opaque to the penetrating beam 19 and indicate second and third calibration points 46 49, respectively. FIG. 6 shows one embodiment of the present invention in which the three calibration targets 42, 45, 48 are on a pad 51 which may be placed on the receiver 13.

As shown in FIG. 4, the present invention also includes a position recorder 54 capable of storing information corresponding to at least two calibration positions of the target axis 24. The position recorder 54 may also be capable of storing other information such as the relative location of the center of emanation 78 of the penetrating beam 19. The position recorder 54 may include a computer. The position recorder 54 may be coupled via transmission lines 56 to position sensors 57 for signaling to the position recorder 54 the values of parameters describing the position of the target axis 24. In lieu of transmission lines 56, the position sensors 57 may signal the information about the position of the target axis 24 to the position recorder 54 via wireless means, including infrared, radio frequency, and other means of transmitting signals.

The position sensors 57 may be stepper motors. When stepper motors are used, the targeting assembly 16 is initially set in a known position. As a stepper motor moves the targeting assembly 16, the position recorder 54 records the net number of steps in a particular direction that have occurred since the stepper motor was in the initial position. The net number of steps is correlated to a position of the target axis 24.

The present invention also includes a calculator 60 (see FIG. 4) in communication with the position recorder 54 and the sensors 57. The calculator 60 is capable of determining a desired position of the target axis 24 with respect to at least one degree of freedom, given the position of the targeting point 26 with respect to at least one other degree of freedom, and given information on the relative location of the center of emanation 78 of the penetrating beam 19. For example, given the position of the targeting point 26 in one of the translatable degrees of freedom, and given information on the relative location of the center of emanation 78 of the penetrating beam 19, the calculator 60 is capable of determining the desired position of the target axis 24 in one of the rotational degrees of freedom. The desired position of the target axis 24 is one that is aligned with a ray of the penetrating beam 19 that passes through the targeting point 26. As will be seen later, the effect of aligning the target axis 24 with a ray of the penetrating beam 19 is to target an area of interest with the targeting beam 31.

The calculator 60 may be a computer having software running thereon. The software may utilize the information corresponding to the at least two calibration positions recorded in the position recorder 54 to effectively determine the location of the point which is the center of emanation 78 of the penetrating beam 19 with respect to a frame of reference. Alternatively, the relative location of the center of emanation 78 may be determined by other means and stored in the position recorder or otherwise be made available to the calculator.

Knowing the location of the center of emanation 78 of the penetrating beam 19 and the relative position of the targeting point 26 (which lies on the target axis 24) in at least one of the degrees of freedom, the desired position of the target axis 24 in at least one other degree of freedom can be calculated using mathematical equations representing the geometric relationship between the targeting point 26 and the center of emanation 78.

One embodiment of the present invention may be described, as shown in FIGS. 7 through 10, by imagining a frame of reference for the targeting assembly 16 having three mutually orthogonal axes 63, 66, 69 intersecting at a common origin 72, with two of the axes 63, 66 defining a reference plane 75. The location of the center of emanation 78 of the penetrating beam 19 with respect to the reference plane 75 may be described with a set of coordinates that correspond to the three axes 63, 66, 69. For example, the three axes may be referred to as an x-axis 63, a y-axis 66 and a z-axis 69, and the location of the center of emanation 78 of the penetrating beam 19 may be described by an x-coordinate, a y-coordinate and a z-coordinate.

For purposes of further describing the present invention, an embodiment will be further described wherein the targeting point 26 is in the reference plane 75 (see FIGS. 8 through 10), i.e. the targeting point 26 is the location at which the target axis 24 intersects the reference plane 75. The degrees of freedom of the targeting assembly 16 permit the target axis 24 to intersect the reference plane 75 at any location and to lie at a multitude of inclinations with respect to the reference plane 75. In this embodiment of the present invention, in order to fully describe a position of the target axis 24 along which the targeting beam 31 is directed, four descriptive parameters will be used, two translational and two rotational. The two translational parameters, herein referred to as Q and P, correspond to the x-coordinate and the y-coordinate of the targeting point 26. The target axis 24 may be thought of as lying in a plane (herein referred to as the "beam plane" 81) defined by the target axis 24 and a rotational axis 84 that lies in the reference plane 75 and is parallel to the y-axis 66. One of the rotational parameters is a beam plane angle $\alpha$, which is the angle between the beam plane 81 and the reference plane 75. A second rotational parameter is a target axis angle $\beta$, which is the angle within the beam plane 81, between the target axis 24 and the rotational axis 84. For any given position of the target axis 24, a full description of the position of the target axis 24 with respect to the reference plane 75 is given by the values of Q, P, $\alpha$ and $\beta$. The sensors 57 and position recorder 54 are capable of determining and recording the values of parameters that describe the position of the target axis 24, for example values of parameters corresponding to two translational degrees of freedom (Q,P) and two rotational degrees of freedom ($\alpha$, $\beta$).

A portion of a targeting assembly 16 according to the present invention is shown in FIG. 4. Such a targeting assembly 16 includes a base 85, a first slider block 87, a second slider block 90, a rotating yoke 93 and a rotating cylinder 96. The base 85 is fixed with respect to the reference plane 75. Only a portion of the rotating cylinder 96 is shown in FIG. 4, although an entire rotating cylinder 96 is shown in FIG. 3. The reference plane 75 is not shown in FIG. 4, but may be thought of as lying parallel to the base 85 and intersecting the targeting point 26.

The position sensors 57 produce signals corresponding to the translational locations of the blocks 87, 90, and the angular positions of the yoke 93 and the cylinder 96. The signals produced by the position sensors 57 are detected by the position recorder 54 and the calculator 60, for example via the transmission lines 56. One such position sensor 57 that could be used to detect the position of the blocks 87, 90, is a stepper motor linear actuator, such as model no. 36343-12 manufactured by Haydon Switch and Instrument Company, Inc. of Waterbury, Conn. Another sensor for use with the yoke 93 and cylinder 96 is a stepper motor such as model 26GH1912-44, also manufactured by Haydon Switch and Instrument Company, Inc. of Waterbury, Conn.

Figure 10:
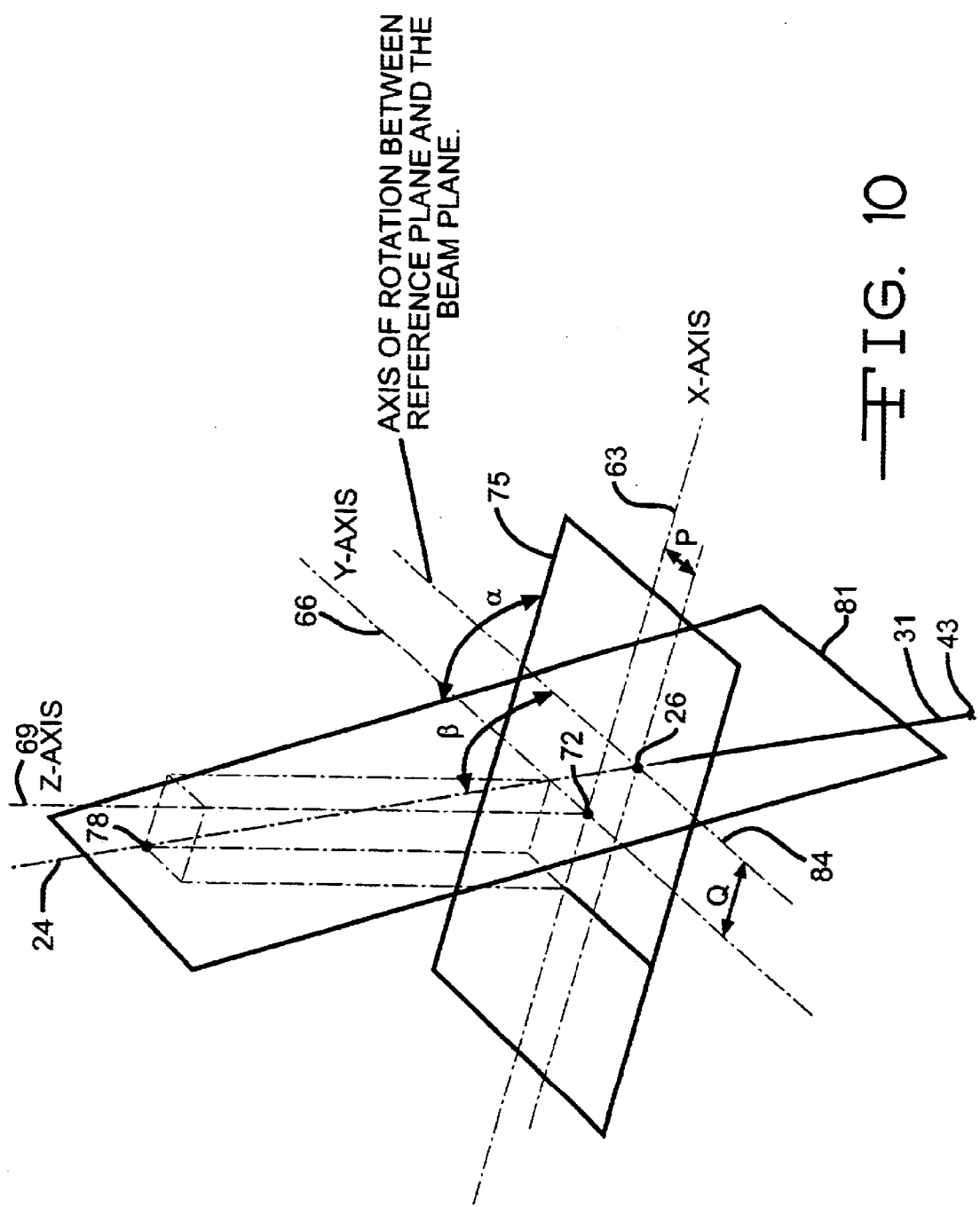

The signal from the position sensors 57 corresponding to the first slider block 87 corresponds to the y-coordinate P, and the signal corresponding to the second slider block 90 corresponds to the x-coordinate Q. The signal corresponding to the angle of the yoke 93 corresponds to the beam plane angle $\alpha$, and the signal corresponding to the angle of the cylinder 96 corresponds to the target axis angle $\beta$. FIG. 10 shows one position of the target axis 24 during calibration i.e. with the target axis 24 in a calibration position, wherein the target axis 24 intersects both the center of emanation 78 of the penetrating beam 19, as well as a calibration point 43.

Calibration

Figure 11A:
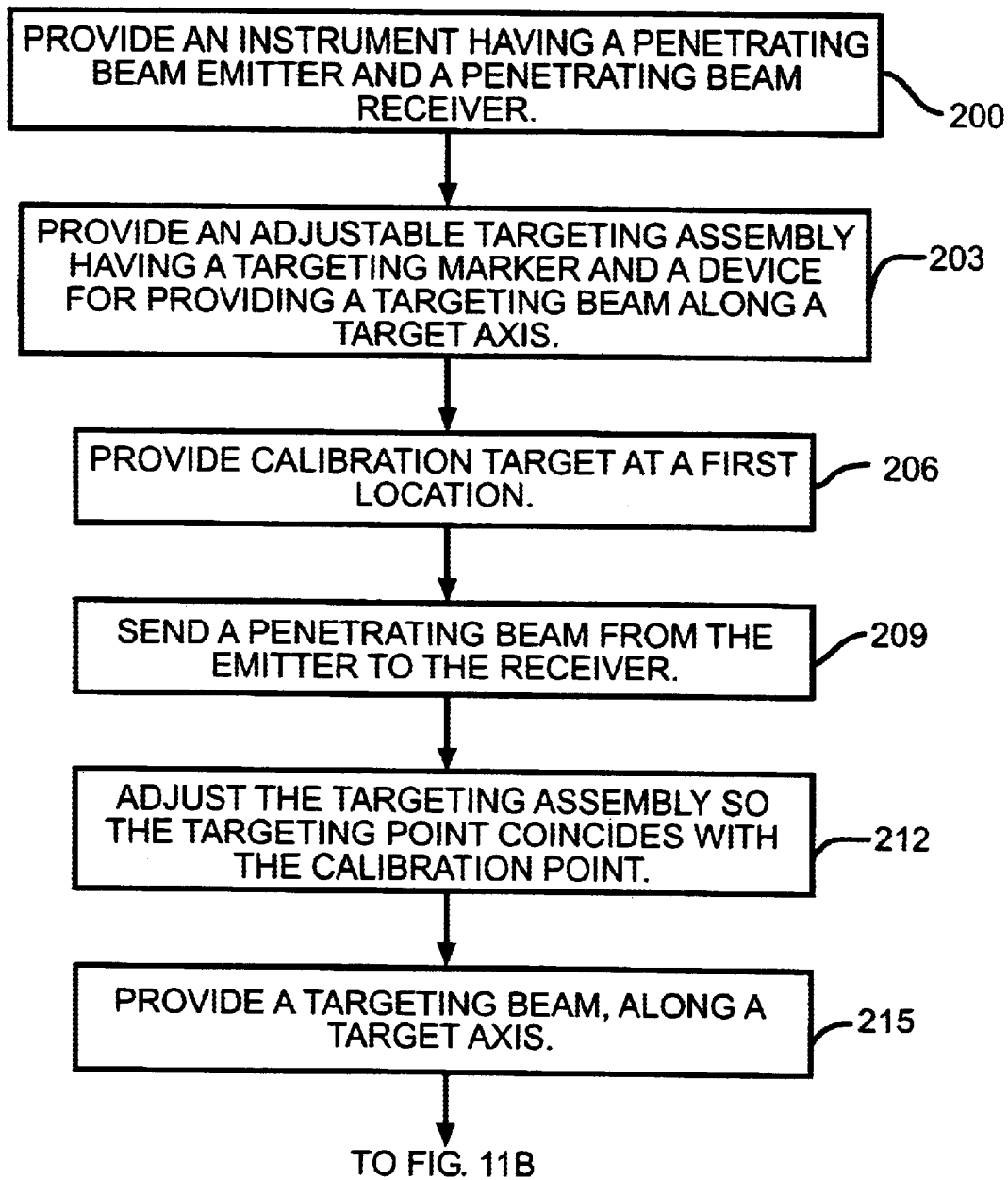
Figure 11B:
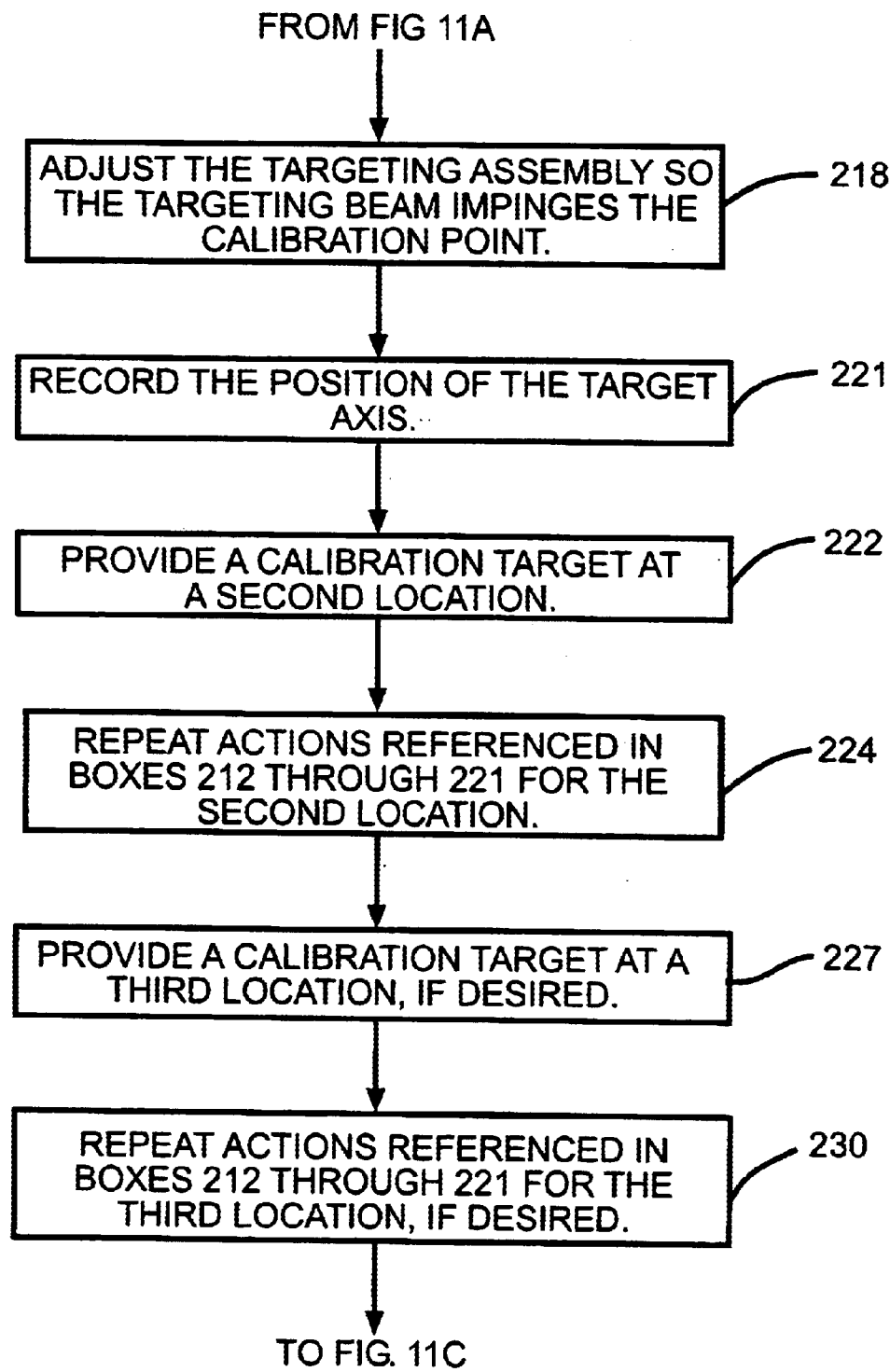

FIGS. 11A through 11C show steps of a method according to the present invention. In the method, a targeting system is operated so as to determine at least two sets of calibration data, each set corresponding to information describing a calibration position of the target axis. For example, a set of calibration data may include Q, P, $\alpha$ and $\beta$. The two sets of calibration data are used to effectively determine the location of the center of emanation 78 of the penetrating beam 19 with respect to the reference plane 75. One skilled in the art will recognize that two full sets of calibration data need not be obtained, for example, one full set and one partial set of calibration data could be sufficient to determine the center of emanation 78 of the penetrating beam 19. In the method, an instrument having a penetrating beam emitter 10 and a penetrating beam receiver 13 is provided 200. An adjustable targeting assembly, such as that described above, is provided 203. The targeting assembly is adjustable in at least four degrees of freedom. For example, the targeting assembly may be translatable such that a targeting point can be moved within a reference plane, and so that a targeting beam that is directed along a target axis passing through the targeting point can be rotated around two rotational axes, one of which is in the reference plane.

The method includes providing a calibration target 206 at a first location within the path of the penetrating beam, for example on the receiver. The calibration target is at least partially opaque to the penetrating beam and indicates a calibration point. A penetrating beam is sent 209 by the penetrating beam emitter toward and received by the receiver. If necessary, the targeting assembly is initially adjusted 212 so the targeting point is moved in at least one of the degrees of freedom, for example by translating the targeting point, so the image provided by the receiver indicates the targeting point coincides with the calibration point at the first location. Once this is done, the targeting point lies along a ray of the penetrating beam emanating from the emitter to the calibration point. A targeting beam is provided 215 along a target axis by the targeting beam device, and a second adjustment is made 218 to the targeting assembly in at least one of the other degrees of freedom, for example by rotating the targeting assembly, so the targeting beam impinges the calibration point at the first location. In making the second adjustment 218, the targeting assembly is adjusted without moving the targeting point from the ray emanating from the emitter to the calibration point. Note, in one embodiment of the present invention, the targeting point is on the axes of rotation so the translational position of the targeting point is not affected by rotation. Information corresponding to the position of the target axis is recorded 221 as a first calibration position. For example the values for Q, P, $\alpha$ and $\beta$ are recorded as the first calibration position.

Then a calibration target is provided 222 at a second location, for example on the receiver. The calibration target previously provided at the first location may be moved to the second location, or a different calibration target may be provided at the second location. If a different calibration target is provided at the second location, it is at least partially opaque to the penetrating beam and indicates a calibration point. Then, the targeting assembly is adjusted 224/212 in at least one of the degrees of freedom, for example by translating the targeting point, so the image provided by the receiver indicates the targeting point coincides with the calibration point at the second location. The targeting beam is provided 224/215 and the targeting assembly is adjusted 224/218 in at least one of the other degrees of freedom, for example by rotating the targeting assembly, so the targeting beam impinges the calibration point at the second location. As described above, the targeting point remains on the penetrating beam ray extending from the emitter to the calibration point at the second location while the targeting assembly is adjusted. Information corresponding to a position of the target axis is recorded as a second calibration position 224/221.

As a check, or to reduce error when calculating the position of the center of emanation, information corresponding to a third calibration position (or more) may be recorded, in a manner similar to that described above, to provide additional accuracy. A calibration target is provided at a third location 227. One of the calibration targets previously provided at the first or second location may be moved to the third location, or a different calibration target may be provided at the third location. If a different calibration target is provided at the third location, it is at least partially opaque to the penetrating beam and indicates a calibration point. Then, the targeting assembly is adjusted 230/212 in at least one of the degrees of freedom, for example by translating the targeting assembly, so the image provided by the receiver indicates the targeting point coincides with the calibration point at the third location. The targeting beam is provided 230/215, and the targeting assembly is adjusted 230/218 in at least one of the other degrees of freedom, for example by rotating the targeting assembly, so the targeting beam impinges the calibration point at the third location. As described above, the targeting point remains on the penetrating beam ray extending from the emitter to the calibration point at the third location while the targeting assembly is adjusted. Information corresponding to a position of the target axis is recorded 230/221 as a third calibration position.

Recorded information corresponding to at least two calibration positions is used to determine 233 the location of the center of emanation of the penetrating beam with respect to the reference plane. The calculator 60 described above can be used to determine the location of the center of emanation.

Targeting an Area of Interest

Figure 12A:
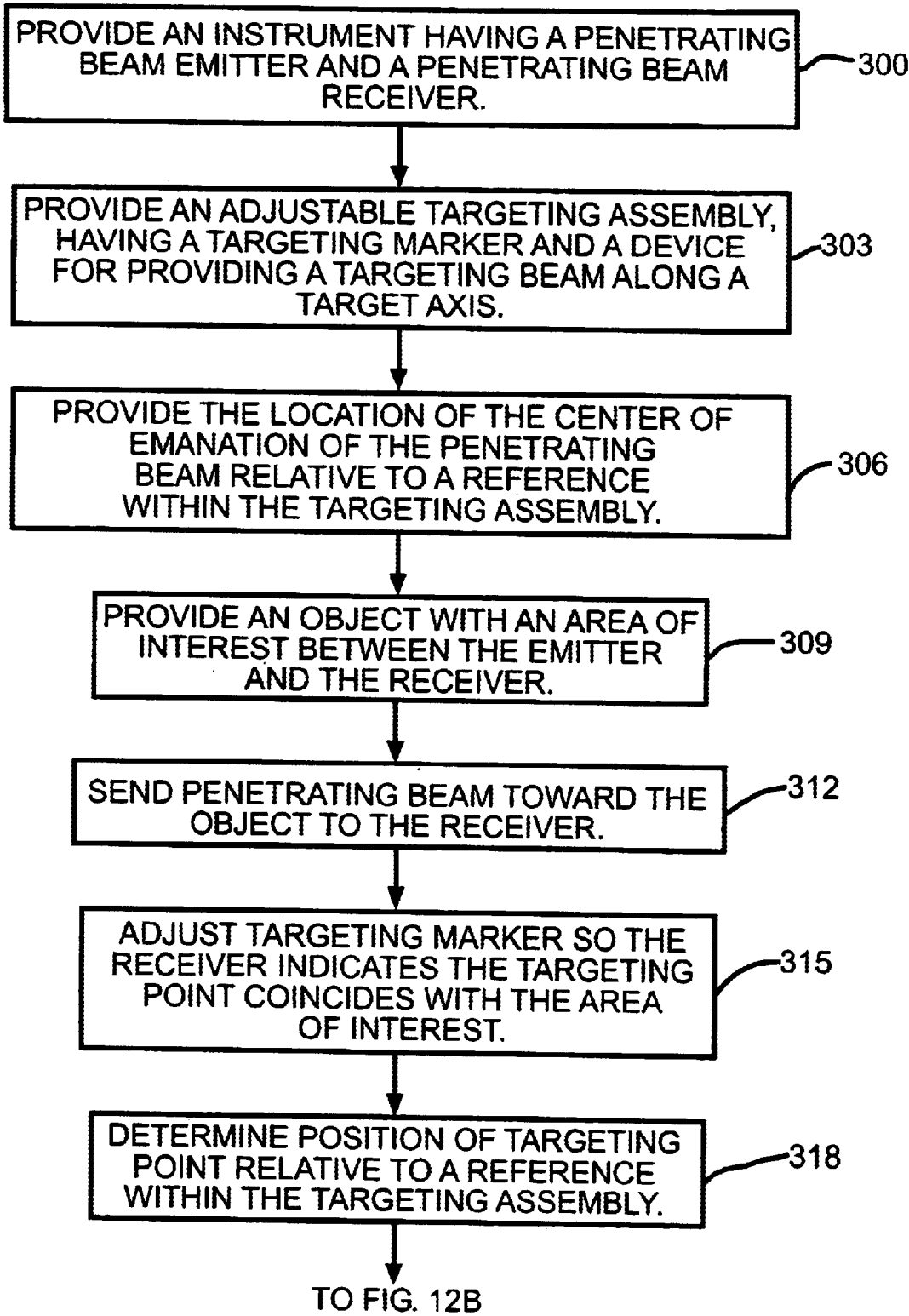
FIGS. 12A and 12B show a method of targeting an area of interest using a system according to the present invention.
Figure 12B:
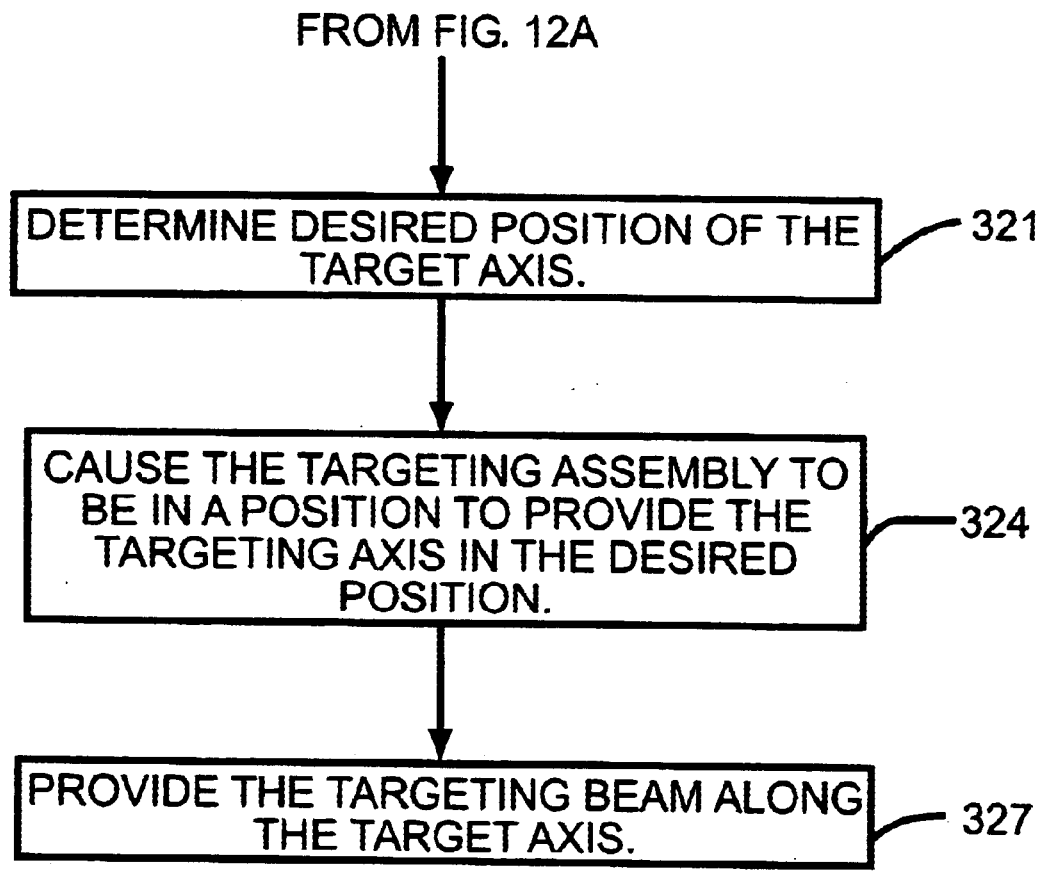

FIGS. 12A and 12B describe a method wherein an instrument with a penetrating beam emitter and a penetrating beam receiver is provided 300 and an adjustable targeting assembly (such as that described above) is provided 303. The relative location of the center of emanation of the penetrating beam is provided 306 (or information sufficient to determine the relative location of the center of emanation, such as information corresponding to two calibration positions of the target axis), and an object is provided 309 in the path of the penetrating beam. The object has an associated area of interest located in the path of the penetrating beam. The object and the area of interest have opacities with respect to the penetrating beam that allow a person to discern the area of interest in the image provided by the receiver. The image provided by the receiver and corresponding to the area of interest may appear darker or lighter than the surrounding portions of the image provided by the receiver. This may be caused by, for example, the area of interest being made from a material different from that of the object, the area of interest having a different density, or the area of interest being a void in the object. In particular, the area of interest may be an unwanted structure, such as a tumor within a human body. It should be noted, the area of interest need not be within the object. For example, a wall may be the object, and the area of interest, a pipe, is behind the wall.

Next, the penetrating beam is sent toward the object and received by the receiver 312. The targeting assembly is adjusted 315 so the image provided by the receiver indicates the targeting point coincides with the area of interest. In this position, the targeting point lies along the ray of the penetrating beam emanating from the emitter to the area of interest. A position of the targeting point with respect to the reference plane in at least one of the degrees of freedom is determined 318, for example via the sensors 57. A corresponding desired position of the target axis with respect to at least one of the other degrees of freedom is determined 321, for example by the calculator 60 described above. Then, the target axis is caused to be in the corresponding desired position, for example by moving 324 the targeting assembly. For example, using the sensors 57, the targeting assembly 16 is adjusted until the sensors 57 indicate the targeting assembly 16 is configured to provide the target axis in the desired determined position. A targeting beam is provided 327 along the target axis so that the targeting beam points toward the area of interest.

It will now be recognized that a device and method according to the present invention may move the targeting point 26 to a desired position, and then adjust the targeting assembly 16 to properly orient the target axis 24, and thus the targeting beam 31. However, a device and method according to the present invention may move the targeting point 26 and adjust the targeting assembly 16 as the targeting point 26 moves to the desired position such that the targeting axis 24 is properly oriented, i.e. intersects the center of emanation 78 of the penetrating beam 19, for each position of the targeting point 26 along the path to the desired position.

The present invention is particularly useful in accurately guiding an instrument, for example a needle, to the area of interest while the penetrating beam 19, an x-ray for example, is turned off. The targeting beam 31, a laser for example, is used to guide the instrument to the area of interest. In this manner, a person is not exposed to the penetrating beam 19, which may be harmful to the person, while guiding an instrument to the area of interest. Also, the area of interest receives less exposure to the penetrating beam, which may be beneficial.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of operating a targeting system, comprising:
   providing an instrument having a penetrating beam emitter and a penetrating beam receiver;
   providing an adjustable targeting assembly including a targeting marker in a path of a penetrating beam of the emitter, the targeting marker being at least partially opaque to a penetrating beam emitted by the emitter, and the targeting marker indicating a targeting point on a target axis, the targeting assembly further including a targeting beam device that is capable of providing a targeting beam along the target axis;
   providing a first calibration target indicating a first calibration point at a first location in the path of the penetrating beam, the first calibration target being at least partially opaque to the penetrating beam;
   sending the penetrating beam toward the receiver;
   receiving the penetrating beam at the receiver;
   providing the targeting beam along the target axis;
   adjusting the targeting assembly so the targeting beam impinges the first calibration point at the first location, and so an image provided by the receiver indicates the targeting point coincides with the first calibration point at the first location;
   recording information corresponding to a position of the target axis as a first calibration position;
   providing a second calibration target indicating a second calibration point at a second location in the path of the penetrating beam, the second calibration target being at least partially opaque to the penetrating beam;
   adjusting the targeting assembly so the targeting beam impinges the second calibration point at the second location, and so an image provided by the receiver indicates the targeting point coincides with the second calibration point at the second location; and
   recording information corresponding to a position of the target axis as a second calibration position.

2. The method of claim 1, wherein the targeting beam is a laser beam.

3. The method of claim 1, wherein the penetrating beam is an x-ray beam.

4. The method of claim 1, wherein the targeting marker includes a first wire, and includes a second wire substantially perpendicular to the first wire.

5. The method of claim 1, wherein adjusting the targeting assembly so the image provided by the receiver indicates the targeting point coincides with any one of the calibration points includes translating at least a part of the targeting assembly.

6. The method of claim 1, wherein adjusting the targeting assembly so the receiver indicates the targeting point coincides with any one of the calibration points includes rotating at least a part of the targeting assembly.

7. The method of claim 1, wherein adjusting the targeting assembly so the targeting beam impinges any one of the calibration points includes rotating at least a part of the targeting assembly.

8. The method of claim 1, wherein adjusting the targeting assembly so the targeting beam impinges any one of the calibration points includes translating at least a part of the targeting assembly.

9. The method of claim 1, wherein the targeting beam device includes a laser positioned on a second axis and a mirror positioned on the target axis and the second axis.

10. The method of claim 9, wherein the mirror is at least partially translucent to the penetrating beam.

11. The method of claim 1, wherein the targeting point is on a rotational axis of the targeting assembly.

12. The method of claim 1, wherein the targeting point is on a translational axis of the targeting assembly.

13. The method of claim 1, further comprising determining a center of emanation of the penetrating beam using at least part of the recorded first calibration position and at least part of the recorded second calibration position.

14. A method of operating a targeting system, comprising:
  providing an instrument having a penetrating beam emitter and a penetrating beam receiver;
  providing an adjustable targeting assembly including a targeting marker in a path of a penetrating beam of the emitter, the targeting marker being at least partially opaque to a penetrating beam emitted by the emitter, and the targeting marker indicating a targeting point on a target axis, the targeting assembly further including a targeting beam device that is capable of providing a targeting beam along the target axis;
  providing an object in the path of the penetrating beam, the object having an associated area of interest located in the path of the penetrating beam, the area of interest and the object having opacities with respect to the penetrating beam that allow a person to discern the area of interest in an image provided by the receiver when the penetrating beam is sent toward the area of interest and received by the receiver;
  sending the penetrating beam toward the object and the area of interest;
  receiving the penetrating beam at the receiver;
  adjusting the targeting assembly so an image provided by the receiver indicates the targeting point coincides with the area of interest;
  determining a position of the targeting point;
  determining a desired position of the target axis;
  adjusting the targeting assembly so the target axis is in the desired position; and
  providing the targeting beam along the target axis.

15. The method of claim 14, wherein the targeting beam is a laser beam.

16. The method of claim 14, wherein the penetrating beam is an x-ray beam.

17. The method of claim 14, wherein the targeting marker includes a first wire, and includes a second wire substantially perpendicular to the first wire.

18. The method of claim 14, wherein adjusting the targeting assembly so the image provided by the receiver indicates the targeting point coincides with the area of interest includes translating at least a part of the targeting assembly.

19. The method of claim 14, wherein adjusting the targeting assembly so the image provided by the receiver indicates the targeting point coincides with the area of interest includes rotating at least a part of the targeting assembly.

20. The method of claim 14, wherein the targeting beam device includes a laser positioned on a second axis and a mirror positioned on the target axis and the second axis.

21. The method of claim 20, wherein the mirror is at least partially translucent to the penetrating beam.

22. The method of claim 14, wherein the targeting point is on a rotational axis of the targeting assembly.

23. The method of claim 14, wherein the targeting point is on a translational axis of the targeting assembly.

24. The method of claim 14, wherein adjusting the targeting assembly so the target axis is in the desired position includes rotating at least a part of the targeting assembly.

25. The method of claim 14, wherein adjusting the targeting assembly so the target axis is in the desired position includes translating at least a part of the targeting assembly.

26. A method of operating a targeting system, comprising:
  providing an instrument having a penetrating beam emitter and a penetrating beam receiver;
  providing an adjustable targeting assembly including a targeting marker in a path of a penetrating beam of the emitter, the targeting marker being at least partially opaque to a penetrating beam emitted by the emitter, and the targeting marker indicating a targeting point on a target axis, the targeting assembly further including a targeting beam device that is capable of providing a targeting beam along the target axis;
  providing a calibration target indicating a calibration point at a first location in the path of the penetrating beam, the calibration target being at least partially opaque to the penetrating beam;
  sending the penetrating beam toward the receiver;
  receiving the penetrating beam at the receiver;
  providing the targeting beam along the target axis;
  adjusting the targeting assembly so the targeting beam impinges the calibration point at the first location, and so an image provided by the receiver indicates the targeting point coincides with the calibration point at the first location;
  recording information corresponding to a position of the target axis as a first calibration position;
  moving the calibration target to a second location in the path of the penetrating beam;
  adjusting the targeting assembly so the targeting beam impinges the calibration point at the second location, and so an image provided by the receiver indicates the targeting point coincides with the calibration point at the second location; and
  recording information corresponding to a position of the target axis as a second calibration position.

27. The method of claim 26, wherein the targeting beam is a laser beam.

28. The method of claim 26, wherein the penetrating beam is an x-ray beam.

29. The method of claim 26, wherein the targeting marker includes a first wire, and includes a second wire substantially perpendicular to the first wire.

30. The method of claim 26, wherein adjusting the targeting assembly so the image provided by the receiver indicates the targeting point coincides with the calibration point includes translating at least a part of the targeting assembly.

31. The method of claim 26, wherein adjusting the targeting assembly so the receiver indicates the targeting point coincides with the calibration point includes rotating at least a part of the targeting assembly.

32. The method of claim 26, wherein adjusting the targeting assembly so the targeting beam impinges the calibration point includes rotating at least a part of the targeting assembly.

33. The method of claim 26, wherein adjusting the targeting assembly so the targeting beam impinges the calibration point includes translating at least a part of the targeting assembly.

34. The method of claim 26, wherein the targeting beam device includes a laser positioned on a second axis and a mirror positioned on the target axis and the second axis.

35. The method of claim 34, wherein the mirror is at least partially translucent to the penetrating beam.

36. The method of claim 26, wherein the targeting point is on a rotational axis of the targeting assembly.

37. The method of claim 26, wherein the targeting point is on a translational axis of the targeting assembly.

38. The method of claim 26, further comprising determining a center of emanation of the penetrating beam using at least part of the recorded first calibration position and at least part of the recorded second calibration position.

39. A targeting system, comprising:
   a penetrating beam emitter;
   a penetrating beam receiver;
   an adjustable targeting assembly, the targeting assembly including a targeting marker in a path of a penetrating beam provided by the emitter, the targeting marker being at least partially opaque to a penetrating beam emitted by the emitter, and the targeting marker indicating a targeting point on a target axis, the targeting assembly further including a targeting beam device capable of providing a targeting beam along the target axis;
   a first calibration target indicating a calibration point located in the path of the penetrating beam, the first calibration target being at least partially opaque to the penetrating beam;
   a second calibration target indicating a second calibration point located in the path of the penetrating beam, the second calibration target being at least partially opaque to the penetrating beam;
   the targeting assembly being adjustable so that the targeting beam impinges the first and second calibration points, respectively; and
   a position recorder capable of recording information corresponding to at least two calibration positions of the target axis.

40. The system of claim 39, wherein the targeting beam is a laser beam.

41. The system of claim 39, wherein the penetrating beam is an x-ray beam.

42. The system of claim 39, wherein the targeting marker includes a first wire, and includes a second wire substantially perpendicular to the first wire.

43. The system of claim 39, wherein the position recorder includes a computer and software for running on the computer.

44. The system of claim 39, wherein the targeting beam device includes a laser positioned on a second axis and a mirror positioned on the target axis and the second axis.

45. The system of claim 44, wherein the mirror is at least partially translucent to the penetrating beam.

46. The system of claim 39, wherein the targeting point is on a rotational axis of the targeting assembly.

47. The system of claim 39, wherein the targeting point is on a translational axis of the targeting assembly.

48. A targeting system, comprising:
   a penetrating beam emitter;
   a penetrating beam receiver;
   an adjustable targeting assembly, the targeting assembly including a targeting marker in a path of a penetrating beam emitted by the emitter, the targeting marker being at least partially opaque to a penetrating beam emitted by the emitter, and the targeting marker indicating a targeting point on a target axis, the targeting point having a first position in a first degree of freedom and a second position in a second degree of freedom, the targeting assembly further including a targeting beam device capable of providing a targeting beam along the target axis, the targeting assembly being adjustable so that the targeting beam impinges on the first and second positions, respectively; and
   a calculator capable of determining a desired position of the target axis in a first degree of freedom given a position of the targeting point in a second degree of freedom, and given information sufficient to determine a location of the center of emanation of the penetrating beam.

49. The system of claim 48, wherein the calculator includes a computer and software for running on the computer.

50. The system of claim 48, wherein the targeting beam is a laser beam.

51. The system of claim 48, wherein the penetrating beam is an x-ray beam.

52. The system of claim 48, wherein the targeting marker includes a first wire, and includes a second wire substantially perpendicular to the first wire.

53. The system of claim 48, wherein the targeting beam device includes a laser positioned on a second axis and a mirror positioned on the target axis and the second axis.

54. The system of claim 53, wherein the mirror is at least partially translucent to the penetrating beam.

55. The system of claim 48, wherein the targeting point is on a rotational axis of the targeting assembly.

56. The system of claim 48, wherein the targeting point is on a translational axis of the targeting assembly.

57. A method of operating a targeting system, comprising:
   providing an instrument having a penetrating beam emitter and a penetrating beam receiver;
   providing an adjustable targeting assembly having at least four degrees of freedom, the targeting assembly including a targeting marker in a path of a penetrating beam provided by the emitter, the targeting marker being at least partially opaque to a penetrating beam emitted by the emitter, and the targeting marker indicating a targeting point on a target axis, the targeting assembly further including a targeting beam device capable of providing a targeting beam along the target axis;
   providing a first calibration target indicating a first calibration point at a first location and a second calibration target indicating a second calibration point at a second location, the first and second calibration points being located on a path of a penetrating beam provided by the emitter, the first and second calibration targets being at least partially opaque to the penetrating beam;
   sending the penetrating beam toward the receiver;
   receiving the penetrating beam at the receiver;
   providing the targeting beam along the target axis;
   adjusting the targeting assembly in at least one of the degrees of freedom so the targeting beam impinges the first calibration point at the first location, and so an image provided by the receiver indicates the targeting point coincides with the first calibration point at the first location;
   recording information corresponding to a position of the target axis as a first calibration position;

adjusting the targeting assembly in at least one of the degrees of freedom so the targeting beam impinges the second calibration point at the second location, and so an image provided by the receiver indicates the targeting point coincides with the second calibration point at the second location; and recording information corresponding to a position of the target axis as a second calibration position.

58. The method of claim 57, wherein the targeting beam is a laser beam.

59. The method of claim 57, wherein the penetrating beam is an x-ray beam.

60. The method of claim 57, wherein the targeting marker includes a first wire, and includes a second wire substantially perpendicular to the first wire.

61. The method of claim 57, wherein adjusting the targeting assembly so the image provided by the receiver indicates the targeting point coincides with any one of the calibration points includes translating at least a part of the targeting assembly.

62. The method of claim 57, wherein adjusting the targeting assembly so the image provided by the receiver indicates the targeting point coincides with any one of the calibration points includes rotating at least a part of the targeting assembly.

63. The method of claim 57, wherein adjusting the targeting assembly so the targeting beam impinges any one of the calibration points includes rotating at least a part of the targeting assembly.

64. The method of claim 57, wherein adjusting the targeting assembly so the targeting beam impinges any one of the calibration points includes translating at least a part of the targeting assembly.

65. The method of claim 57, wherein the targeting beam device includes a laser positioned on a second axis and a mirror positioned on the target axis and the second axis.

66. The method of claim 65, wherein the mirror is at least partially translucent to the penetrating beam.

67. The method of claim 57, wherein the targeting point is on a rotational axis of the targeting assembly.

68. The method of claim 57, wherein the targeting point is on a translational axis of the targeting assembly.

69. The method of claim 57, further comprising determining a center of emanation of the penetrating beam using at least part of the recorded first calibration position and at least part of the recorded second calibration position.

70. A method of operating a targeting system, comprising:
providing an instrument having a penetrating beam emitter and a penetrating beam receiver;
providing an adjustable targeting assembly having at least tour degrees of freedom, the targeting assembly including a targeting marker in a path of a penetrating beam provided by the emitter, the targeting marker being at least partially opaque to a penetrating beam emitted by the emitter, and the targeting marker indicating a targeting point on a target axis, the targeting assembly further including a targeting beam device capable of providing a targeting beam along the target axis;
providing a object in the path of the penetrating beam, the object having an associated area of interest located in the path of the penetrating beam, the area of interest and the object having opacities with respect to the penetrating beam that allow a person to discern the area of interest in an image provided by the receiver when the penetrating beam is sent toward the area of interest and received by the receiver;
sending the penetrating beam toward the object and the area of interest;
receiving the penetrating beam at the receiver;
adjusting the targeting assembly in at least one of the degrees of freedom so an image provided by the receiver indicates the targeting point coincides with the area of interest;
determining a position of the targeting point in at least one of the degrees of freedom;
determining a desired position of the target axis in at least one of the degrees of freedom;
adjusting the targeting assembly so the target axis is in the desired position; and
providing the targeting beam along the target axis.

71. The method of claim 70, wherein the targeting beam is a laser beam.

72. The method of claim 70, wherein the penetrating beam is an x-ray beam.

73. The method of claim 70, wherein the targeting marker includes a first wire, and includes a second wire substantially perpendicular to the first wire.

74. The method of claim 70, wherein the targeting beam device includes a laser positioned on a second axis and a mirror positioned on the target axis and the second axis.

75. The method of claim 74, wherein the mirror is at least partially translucent to the penetrating beam.

76. The method of claim 70, wherein the targeting point is on a rotational axis of the targeting assembly.

77. The method of claim 70, wherein the targeting point is on a translational axis of the targeting assembly.

78. The method of claim 70, wherein adjusting the targeting assembly so the image provided by the receiver indicates the targeting point coincides with the area of interest includes translating at least a part of the targeting assembly.

79. The method of claim 70, wherein adjusting the targeting assembly so the image provided by the receiver indicates the targeting point coincides with the area of interest includes rotating at least a part of the targeting assembly.

80. The method of claim 70, wherein determining a position of the targeting point in at least one of the degrees of freedom includes determining a translational position of the targeting point.

81. The method at claim 70, wherein determining a position of the targeting point in at least one of the degrees of freedom includes determining a rotational position of the targeting point.

82. The method of claim 70, wherein adjusting the targeting assembly so the target axis is in the desired position includes rotating at least a part of the targeting assembly.

83. The method of claim 70, wherein adjusting the targeting assembly so the target axis is in the desired position includes translating at least a part of the targeting assembly.

84. A targeting system, comprising:
a penetrating beam emitter;
a penetrating beam receiver;
an adjustable targeting assembly having at least four degrees of freedom, the targeting assembly including a targeting marker on a path of a penetrating beam provided by the emitter, the targeting marker being at least partially opaque to a penetrating beam emitted by the emitter, and the targeting marker indicating a targeting point on a target axis, the targeting assembly further including a targeting beam device capable of providing a targeting beam along the target axis.

85. The system of claim 84, further comprising:
a calibration target located in the path of the penetrating beam provided by the emitter, the calibration target indicating a calibration point and being at least partially opaque to the penetrating beam; and a position recorder capable of recording information corresponding to at least two calibration positions of the target axis.

86. The system of claim 85, wherein the position recorder includes a computer and software for running on the computer.

87. The system of claim 84, wherein the targeting beam is a laser beam.

88. The system of claim 84, wherein the penetrating beam is an x-ray beam.

89. The system of claim 84, wherein the targeting marker includes a first wire, and includes a second wire substantially perpendicular to the first wire.

90. The system of claim 84, wherein the targeting beam device includes a laser positioned on a second axis and a mirror positioned on the target axis and the second axis.

91. The system of claim 90, wherein the mirror is at least partially translucent to the penetrating beam.

92. The system of claim 84, further including a calculator capable of determining a desired position of the target axis in a first one of the degrees of freedom given the position of the targeting point in a second one of the degrees of freedom and given information sufficient to determine a location of a center o emanation of the penetrating beam.

93. The system of claim 92, wherein the calculator includes a computer and software for running on the computer.

94. The system of claim 84, wherein the targeting point is on a rotational axis of the targeting assembly.

95. The system of claim 84, wherein the targeting point is on a translational axis of the targeting assembly.

* * * * *